United States Patent [19]
Bonnefous

[11] Patent Number: 5,411,028
[45] Date of Patent: May 2, 1995

[54] DEVICE AND METHOD FOR MEASURING THE ELASTICITY OF AN ARTERY BY ULTRASONIC ECHOGRAPHY

[75] Inventor: Odile Bonnefous, Nogent-sur-Marne, France

[73] Assignee: U.S. Philips Corporation, New York, N.Y.

[21] Appl. No.: 173,330

[22] Filed: Dec. 21, 1993

[30] Foreign Application Priority Data

Dec. 22, 1992 [FR] France .................. 92 15506

[51] Int. Cl.⁶ .............................................. A61B 8/00
[52] U.S. Cl. ........................... 128/661.08; 128/660.02
[58] Field of Search .................. 128/660.01, 660.02, 128/660.06, 661.08, 661.09, 661.10, 662.06

[56] References Cited

U.S. PATENT DOCUMENTS

| | | | |
|---|---|---|---|
| 4,803,990 | 2/1989 | Bonnefous et al. | 128/661.08 |
| 5,107,840 | 4/1992 | Bonnefous et al. | 128/661.08 |
| 5,203,337 | 4/1993 | Feldman | 128/660.01 |
| 5,265,612 | 11/1993 | Sarvazyan et al. | 128/662.06 |
| 5,307,816 | 5/1994 | Hashimoto et al. | 128/662.06 |

FOREIGN PATENT DOCUMENTS

0458384 11/1991 European Pat. Off. .
2156985 10/1985 United Kingdom .

*Primary Examiner*—George Manuel
*Attorney, Agent, or Firm*—Jack D. Slobod

[57] ABSTRACT

An ultrasonic echograph is used as a profilometer for the measurement of the instantaneous blood flow rate Q(t) and the instantaneous radius variation Δr(t) and the mean radius $r_0$ of the artery along a first excitation line A. In accordance with the invention, the profilometer is conceived to supply also Q'(t) and Δr'(t) along a second excitation line B which is situated at a distance e, of the order of magnitude of millimeters, from the first line. This collection of data enables, by calculation, determination of the elasticity or compliance γ(t) of the artery and its internal pressure P(t) at the area of measurement.

9 Claims, 2 Drawing Sheets

DEVICE AND METHOD FOR MEASURING THE ELASTICITY OF AN ARTERY BY ULTRASONIC ECHOGRAPHY

FIELD OF THE INVENTION

The invention relates to a device and a method for measuring physiological parameters of an artery tinder the effect of the blood pressure P comprising, in an ultrasonic echograph used in the profilometer mode (M mode) and provided with transmission/receiving means including a device for forming channels in the receiving mode, a first assembly for measurement and calculation of the instantaneous blood flow rate Q(t), of the instantaneous variation of the radius $\Delta r(t)$ of the artery, and of its mean radius $r_0$ along a first excitation line A.

The circulatory system has long been studied and described very well. The data have been collected by in vivo and in vitro measurements on animal or human objects, but most of the time in an invasive or traumatic manner. However, the new ultrasonic tools can enable non-invasive in vivo measurements as, for example, using pulsed Doppler techniques.

BACKGROUND OF THE INVENTION

The time correlation methods used in the CVI (Colour Velocity Imaging) technique enable definition of measurements and measuring tools which are adapted to the mechanical characterization of arteries. The prior-art technological background in this field is formed mainly by scientific works describing the circulatory system as well as the means previously used to study it, for example:
McDonald's Blood flow in Arteries, by W. W. Nichols and M. F. O'Rourke, edited by Edward Arnold, London.

A device of the kind set forth is known notably from European Patent Application No. 0 458 384 A1 in the name of applicant which corresponds to U.S. Pat. No. 5,107,840 and is incorporated herein by way of reference. Such a device is preferably used for the echographic examination of blood flows in vessels, notably for diagnostic measurement and display of characteristic physiological parameters of these flows.

An embodiment of the device in accordance with the cited application comprises a first unit for measuring, using ultrasonic echography, the speed V(t,z) of the blood flow as a function of time t and of scanning depth z, the measurement of the speed V(t,z) being independent of the ultrasonic wave used, and also comprises a memory for storing samples of the speed V(t,z). This embodiment is characterized in that it also comprises a combination of first circuits for calculating the instantaneous flow rate Q(t) from said samples of the speed V(t,z) as well as a second unit for measuring the radial speeds $V_1(t,z)$ and $V_2(t,z)$ of shift of the two vessel walls diametrically bounding said blood flow, memories for storing the speed values $V_1(t,z)$ and $V_2(t,z)$, second calculating circuits comprising a circuit for calculating the local energy wherefrom the fixed echos $E_2(t,z)$ have not been removed, followed by a circuit for calculating respective thicknesses $d_1 = z_4 - z_3$ and $d_2 = z_6 - z_5$ of said walls, formed by a threshold detector with the value $E'_0$ for the determination of the values $z_3, z_4, z_5, z_6$, two circuits for calculating respective mean speeds $\hat{V}_1(t_0)$ et $\hat{V}_2(t_0)$ of said walls for each time value $t_0$, formed by an adder giving $\Sigma_{d1} V_1(t,z)$ (or $\Sigma_{d2} V_2(t,z)$) and by a divider by $M_1$ (or $M_2$), $M_1$ and $M_2$ being the number of measuring samples on the segment $[z_3, z_4]$ (or $[z_5, z_6]$), a circuit for calculating the shift of each wall which is formed by an adder supplying:

$$D_1(t) = \Sigma_t \hat{V}_1(t_0) \text{ and } D_2 = \Sigma_t \hat{V}_2(t_0),$$

and a circuit for calculating the symmetrical shift of the walls which is formed by a subtracter and a divider-by-2 and which supplies, in the form of time samples, the instantaneous radius variation $\Delta r(t) = (D_2(t) - D_1(t))/2$ of said vessel, and means for displaying the curves Q(t) and $\Delta r(t)$ as a function of time t.

Because notably the flow rate Q(t) and the radius variation $\Delta r(t)$ of the vessel of an artery are known simultaneously, various calculations can be performed and several highly useful representations can be realised. Actually, the function $\Delta r(t)$ can be considered to be an image of the pressure P(t) prevailing in the vessel in a sense that, the dilation of the vessel being a direct function of the pressure, the increasing and decreasing phases of these two functions are the same in the course of the cardiac cycle. Therefore, in a first approximation it is permissible to equate P(t) with $\Delta r(t)$, except for a proportionality factor.

A particularly interesting combined mode of representation of the flow rate and the pressure variation consists in calculating and displaying the curve of the cardiac cycle, parameterised as a function of time and retrocoupled to itself, which is formed by the points obtained by plotting on the ordinates the sample values of the function $\Delta r(t)$ and on the abscissae the sample values of the instantaneous flow rate function Q(t), the product $Q \times \Delta r$, being a part of the plane of display, then being homogeneous for one power in a first approximation.

On the basis of the measurement of the surface of the cycle and of the surface subtended by the cycle, notably the calculation of the arterial efficiency for the slice of axial thickness dx of the vessel analysed can thus be deduced.

The efficiency calculation, expressed by power ratios and, over the duration of a cycle or a part of a cycle, by energy ratios, directly reflects the energy lost in the part of the vessel analysed during a cycle and hence the roughness and/or the local constriction of the wall of the vessel; this is a precious tool for the detection of stenoses. Moreover, the representation in a loop as described above reveals, for each type of artery, a very characteristic shape which resembles a "signature" and it is imaginable that on the basis of experience such a characteristic shape could be interpreted by the radiologist as revealing a pathology of the heart and/or the artery analysed.

The use of the representation mode given above, and of given other modes, requires highly accurate determination of the functions Q(t) and $\Delta r(t)$.

Among the ultrasonic echographs whereby such a high precision can be achieved and which notably can provide, upstream, a measurement of blood flow speeds which is independent of the ultrasonic frequency, there are those which operate according to the time correlation principle already described in European Patent Application No. 0 225 667 in the name of applicant which corresponds to U.S. Pat. No. 4,803,990 and whose unit for measuring the flow speed comprises a correlation circuit which delivers correlation function values, on the basis of two successive echos, and also a multiplexing/interpolation circuit which supplies an estimate of the speed V(t,z) on the basis of said correlation function values.

In the event of a state of the art as described above, it could be desirable to determine parameters, as a function of time, which are very characteristic of hydrodynamic phenomena occurring in an artery. More specifically, it is proposed to determine the elasticity $\gamma$ and the pressure P at an arbitrary point of an artery, be it in the first place the mean values $\gamma_0$ and $P_0$ of these parameters over the duration of a cardiac cycle and, if possible, their variation in time, i.e. the functions $\gamma(t)$ and $P(t)$. The elasticity of an artery can be defined by the differential relation $\gamma = dr/dP$ and is also referred to as compliance. A description thereof can be found in the article "Measure de la compliance artérielle" by Georges Nicod, EPFL (Ecole Polytechnique Fédérale de Lausanne), Presse et information, in relation to the pressure variations in the artery. The cited article also describes a method of determining the compliance in relation to the pressure. The arterial pressure is continuously measured by a photoplethysmograph which measures the pressure differences at the extremity of a finger. Moreover, the diameter of the artery at the point of analysis is determined by an ultrasonic transducer in the pulsed echo (or echo follower) mode. The application of appropriate dephasing, in relation to the cardiac cycle, between the pressure and diameter sensors enables correction of the phase difference of the two curves obtained and formation of the ratio. This method enables a compliance curve to be obtained which can be expressed in percent of increase of diameter per unit of pressure, related to the pressure. It is thus possible to characterize the behaviour of an arbitrary point of an artery and to deduce therefrom the elasticity of the latter at this point. However, this determination remains approximate because the determination of the blood pressure is not performed locally but always at the same area, that is to say at the end of a finger.

Another article: "Non-invasive measurement of interval diameter of peripheral arteries in cardiac cycle" by MOOSER et al., Journal of Hypertension 1988, 6 (suppl. 4), pp. 179–181, published in Switzerland, reveals how to perform an in vivo high precision measurement of the instantaneous diameter of an artery in a non-invasive manner.

The invention aims to determine the elasticity (compliance) of an artery on the basis of echographic measurements which are integrally performed at a predetermined area of the artery analysed.

It is another object of the invention to determine more accurately the compliance of an artery at a given area of the latter.

SUMMARY OF THE INVENTION

These objects are achieved, and the drawbacks of the prior art are mitigated or eliminated, in that the device for measuring physiological parameters as defined above is characterized in that it also comprises, for the determination of the elasticity $\gamma(t)$ of said artery and the pressure $P(t)$ within the latter, a second assembly for measurement and calculation by ultrasonic echography of the parameters $Q'(t)$ and $\Delta r'(t)$ along a second excitation line B which is situated at a distance e from the first excitation line A, which distance is between some tenths of a millimeter and some millimeters, the two excitation lines A and B traversing the artery according to one of its meridian planes, the distance e being taken in the direction of the axis of the artery, first and second storage means for storing digital samples of signals relating to the blood flows and signals relating to the walls of the artery being connected to the output of said first and second assemblies, as well as calculation means which operate on said digital signal samples.

From the basic equation:

$$R\,Q(t) + L\frac{dQ(t)}{dt} + \frac{\Delta P}{\Delta x} = -\frac{1}{\gamma}\,\frac{\partial r}{\partial x} \qquad (1)$$

in which:

R: hydrodynamic resistance of blood,
$L = L_0 = \rho / \Pi r_0^2$, where $\rho$ is the voluminal mass of blood,
$\Delta P / \Delta x = R Q_0$ is the blood pressure gradient along the artery, and where $\delta r/\delta x$, measurable, is identified as the instantaneous variation of the internal radius over the artery over the distance e, it is possible to calculate, preferably by application of the least squares method, the value of notably the compliance $\gamma$.

During a first step the mean values $R_0$, $R_0 Q_0$ and $\gamma_0$ over a cardiac cycle are calculated after which, by successive iterations, $R(t)$ and $\gamma(t)$ are calculated in the form of constant functions by segments, so a few samples of the two functions in the course of this cycle.

Moreover, the pressure $P(t)$ can also be calculated by integration of the equation to the partial derivatives:

$$\frac{\partial P(t)}{\partial t} = -\frac{1}{\gamma(t)}\,\frac{\partial r(t)}{\partial t} \qquad (2)$$

This function $P(t)$ is obtained except for a constant addition but, as will be seen hereinafter, the correct value of $P(t)$ can become known exactly by determination of the mean value $P_0$ in the course of the cardiac cycle.

A first preferred embodiment of the device in accordance with the invention is characterized in that it comprises transmission/receiving means of an ultrasonic echograph operating according to the time correlation principle and intended to produce ultrasonic images in the two-dimensional mode (2D mode), its detection being limited to two neighbouring excitation lines A and B which are separated by the distance e and taking place in pairs of homologous points of the two excitation lines, as well as means for rephasing the signals received for said two neighbouring excitation lines, which means are integrated in said calculation means.

The two-dimensional or 2D mode, well known in ultrasonic echography for producing images of slices of the patient being examined, utilises electronic scanning for the transmission/reception of adjacent elementary transducers of the probe, to form image lines which succeed one another in time because of the line-wise excitation. In order to carry out the invention, the supply of two neighbouring lines (excitations A and B) suffices; these two lines can be separated by the spacing of the image lines in the 2D mode, so that for example $e_0 = 0.45$ mm, or by several times this spacing, so that for example $e_0 = 4.5$ mm for a jump of 9 image lines. The time shift between the two lines, linked to their spatial shift, must be exactly compensated for in the measurement of samples of given functions, such as notably the time function $\delta r/\delta x$. This compensation becomes manifest as rephasing of the signals received due to the excitations A and B; this can be readily deduced from the exactly known period $\tau$, separating the excitations A and B.

A second preferred embodiment of the invention is characterized in that the device is formed by an ultrasonic echograph operating according to the time correlation principle and used as a profilometer in which the transmission means are suitable to transmit a more powerful and slightly defocused ultrasonic beam in comparison with that of a conventional profilometer, the device incorporating a device for forming double receiving channels to supply, simultaneously and in parallel at the output of the two channel forming devices, the signals of two excitation lines A and B which are separated by the distance e.

In this version, whose operation may be considered as a double M mode, phase locking of the signals received from the two simultaneous excitations A and B is no longer necessary.

In order to achieve the required precision for the two functions r(t) which are physically separated notably by the small distance e, echographs based on the time correlation principle are preferred over conventional Doppler systems because of the poor axial resolution of the latter. A time correlation echograph is described, for example in the cited European Patent Application No. 0 225 667 in previously the name of applicant which corresponds to U.S. Pat. No. 4,803,990.

The echo signals from the excitations A and B being stored in the form of time samples in the memories, the periodic functions $\gamma(t)$ and P(t) can be determined after rephasing, if any, and using data processing calculation means.

A first method for measuring the elasticity $\gamma$ of an artery under the effect of the blood pressure P by means of an ultrasonic echograph suitable to produce the instantaneous blood flow rate Q(t), the instantaneous radius variation $\Delta r(t)$ and the mean radius $r_0$ for two neighbouring, parallel excitation lines A and B traversing the artery according to one of its meridian planes, in order to be carried out by the device in conformity with the described embodiments, said values Q(t), $\Delta r(t)$ and $r_0$ being stored in said first and second storage means, comprises the following steps:

i the calculation, on the basis of one of the two functions Q(t), Q'(t), of the mean value $Q_0$ and the derivative $$\frac{\partial Q(t)}{\partial t}$$

of the one function, ii the calculation, on the basis of the instantaneous values $\Delta r(t)$, $\Delta r'(t)$ for the lines A and B, of the instantaneous value:

$$\delta r(t) = \Delta r(t) - r'(t)$$

iii the determination of the mean values of the elasticity parameter $\gamma$, the hydrodynamic resistance parameter R and the pressure gradient parameter $\Delta P/\Delta x$, i.e. $\gamma_0$, $R_0$ and $R_0 Q_0$, respectively, on the basis of the least-squares method applied, over a cardiac cycle, to the relation:

$$\gamma \left[ R Q(t) + L \frac{\partial Q(t)}{\partial t} + \frac{\Delta P}{\Delta x} \right] = - \frac{\partial r(t)}{\partial x}$$

in which the identification:

$$L = \frac{\rho}{\Pi r_0^2}, \text{ and } \frac{\partial r(t)}{\partial x} = \frac{\delta r(t)}{e}$$

is made.

A second method of measuring the elasticity $\gamma$ of an artery, being deduced from the first method described above, is characterized in that for the determination in segments over at least one cardiac cycle, of the functions $\gamma(t)$ and R(t) the least-squares method is applied again by successive iterations over complementary parts of the cardiac cycle whose number increases from one iteration to the next by taking, for the first iteration, two cardiac half-cycles (and then 4, 8, . . . , parts of cycles for the subsequent iterations), and the relation:

$$\gamma_0(1 + g'(t)) \left[ R_0(1 + R'(t)) Q(t) + L \frac{\partial Q}{\partial t} + R_0 Q_0 \right] = - \frac{\delta r(t)}{e},$$

which supplies for $\gamma$ and R the sampled functions of some samples over the duration of the cardiac cycle.

The calculations to be performed for this second method are more complex and more delicate than for the first method, because given functions of time which are zero on average over the duration of the cardiac cycle are no longer zero on average over a part of a cycle and must, therefore, be taken into account in the calculations involved in the least-squares method.

It is to be noted that it is thus possible to determine the compliance $\gamma(t)$ without knowing the pressure P(t) prevailing in the artery at the area of measurement. The determination of P(t), however, is very desirable per se and also in relation to the functions Q(t) and $\gamma(t)$.

It is another object of the invention to determine the instantaneous pressure P(t), in an arbitrary, predetermined area of an artery analysed, on the basis of instantaneous functions of compliance $\gamma(t)$ and radius r(t) of the artery at the relevant To this end, a method for measuring the pressure $P(t) = P_0 + p(t)$ within an artery, in which the value of r(t) for one of the excitations A or B is determined on the basis of the values $r_0$ and $\Delta r(t)$, compatible with the foregoing methods, is characterized in that the variable part p(t) of the pressure is determined by integration with respect to time of the function with the partial derivatives $P_1$:

$$P_1(t) = \int_t \frac{\partial P}{\partial t} dt = \int_t \frac{1}{\gamma(t)} \frac{\partial r}{\partial t} dt$$

followed by suppression of the continuous component $P_c$ of $P_1(t)$:

$$p(t) = P_1(t) - P_c$$

and that the fixed part $P_0$ (to be added to $p(t)$) is determined by application of the least squares method to the relation:

$$\frac{\partial P}{\partial t} = \frac{1}{r} \frac{\partial T}{\partial t} - \frac{1}{r^2} \frac{\partial r}{\partial t} T$$

in which: $r=r(t)$ and $T=T(t)=r(t) P(t)$,
$T(t)$ being the tension, in a physical sense, exerted by the blood on a circumference of the artery, so that therefrom in a first approximation there is deduced:

$$T_0 = \frac{1}{\gamma_0} \frac{<r \frac{\partial r}{\partial t}><\frac{1}{r}\frac{\partial r}{\partial t}> - <\left(\frac{\partial r}{\partial t}\right)^2>}{<\left(\frac{1}{r}\frac{\partial r}{\partial t}\right)^2> - <\frac{1}{r}\frac{\partial r}{\partial t}>^2},$$

in which the symbols $<>$ indicate the mean value of the function over a cardiac cycle, and:

$$P_0 = T_0/r_0 + P_e$$

$P_e$ being the (constant) pressure outside the artery.

The following description, given with reference to the attached drawings, all given by way of a non-limitative example, will offer a better understanding as to how the invention can be carried out.

DESCRIPTION OF PREFERRED EMBODIMENTS

Figure 1:
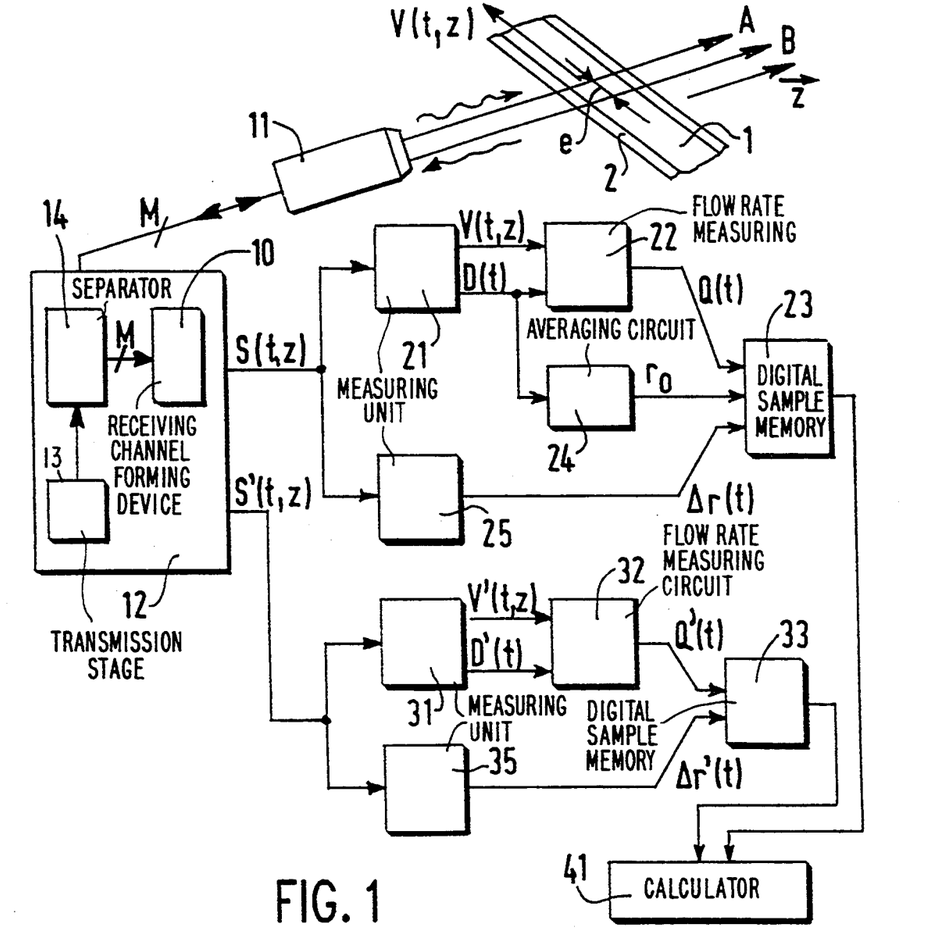
FIG. 1 shows the circuit diagram of an embodiment of the device in accordance with the invention.

The diagram of FIG. 1 represents a device for measuring physiological parameters of a blood flow 1 in an artery 2. The device comprises a piezoelectric transducer 11 which may be, for example an array comprising a plurality of elements. Transmission/receiving means 12, connected to the transducer 11, ensure formation of an ultrasonic scanning beam and a first measuring unit 21 processes the echographic signals returned to the transducer 11 so as to provide estimates of the speed $V(t,z)$ of the flow 1 as a function of time t and the scanning depth $|\bar{z}|$ for a first excitation line A in the direction z.

The transmission/receiving means comprise conventionally at least a transmission stage 13 and a separator 14 for separating the transmission stage 13 and the measuring unit 21. The transmission stage 13 comprises a sequencer which consists of an oscillator and a frequency divider which controls, at the selected recurrent frequency $1/T_r$, a generator whose electric excitation signals are applied to the transducer 11 consisting of a plurality (M) of elementary transducers, which converts said signals into periodic trains of ultrasonic pulse signals. The separator 14 prevents the measuring circuits from being overloaded by the transmission signals and supplies a device 10 for forming receiving channels with the M signals received by the M elementary transducers. An electronic scan control circuit (not shown) for the elementary transducers of the transducer 11 enables selection of any excitation line without displacement of the transducer 11, said lines being situated in the same plane, in a fan-shaped configuration or, as is assumed here, in a parallel configuration. The channel forming device enables the acquisition, by way of specific delay configurations imposed on the signals received from the separator 14, by successive focusing, of as many points as provided along the excitation line chosen at 11, i.e. from the nearest point to the remotest point. The device 10 for forming channels supplies the downstream signal processing circuits with an output signal $S(t,z)$.

The unit 21 for measuring the speed $V(t,z)$ is described in detail in the cited European Patent Application No. 0 458 384 A1. At its input it comprises (not shown) an amplifier and a fixed echo-eliminator which eliminates the major part of the echos originating from walls of the artery analysed. The signal is subsequently processed preferably according to the correlation method described in the cited European Patent Application No. 0 225 667 which utilizes in known manner the time correlation principle, implementing a correlation circuit and preferably a multiplex interpolation circuit.

As opposed to the conventional Doppler velocimeters, the flow speed $V(t,z)$ thus determined offers the advantage that it is insensitive to the dispersion of the ultrasonic wave frequency used, thus enabling much broader use of the results. The values found for the speed $V(t,z)$ are stored, at 21, in a memory for later processing.

The output signal of the fixed-echo eliminator is also utilized, at 21, for determining the diameter $D(t)$ of the flow. On the basis of the instantaneous functions $V(t,z)$ and $D(t)$, a circuit 22 for measuring the instantaneous flow rate $Q(t)$ supplies, based on the two output signals of the unit 21, the information concerning the blood flow rate in the form of digital time samples to the first means 23 for storing digital samples.

The signal $D(t)$ is also applied to the input of an averaging circuit 24 which itself supplies the circuit 23 with digital samples which are representative of the mean internal radius $r_0(t)$ of the artery.

On the basis of the signal $S(t,z)$ it is also possible to perform a high precision measurement of a further physiological parameter, being the instantaneous radius variation $\Delta r(t)$, as described in European Patent Application No. 0 225 667. For the measurement of $\Delta r(t)$ there are provided a second measuring unit 25 for the radial speed $V_1(t,z)$ and $V_2(t,z)$ of the shifting of the two walls of the artery which diametrically bound the blood flow, and other circuits for storage and calculation. At 25 a first chain is formed (in a manner not shown) by a second amplifier, a memory, and subsequently a correlation chain, similar to that indicated above for the measurement of $V(t,z)$. In the present case there is no fixed-echo eliminator, because in this case actually the echo signals originating from the walls are processed, the movements of the walls taking place substantially perpendicularly to the direction of the blood, and the excitation A taking place obliquely in a meridian plane of the artery.

In 25 there are also calculated other characteristic parameters of the artery, resulting in the calculation of the instantaneous radius variation function $\Delta r(t)$. It concerns first of all the thickness of the walls $d_1(t)$ and $d_2(t)$ which are diametrically oppositely situated and whose measurement utilizes, at the output of said second amplifier, a circuit for calculating the local energy and a circuit for calculating the instantaneous wall thicknesses $d_1$ and $d_2$, formed by a detector with an adjustable threshold. The mean speeds $\hat{V}_1(t_0)$ et $\hat{V}_2(t_0)$ of the walls are determined by way of circuits, which are each formed by an adder and a divider. Finally, a second integrator (adders) for integration in time of the mean speed enables the displacement of each wall to be obtained with a high precision:

$$D_1(t) = \sum_{t_0=0}^{t_0=t} \hat{V}_1(t_0)$$

$$D_2(t) = \sum_{t_0=0}^{t_0=t} \hat{V}_2(t_0)$$

The speeds of the walls are very low, i.e. of the order of 0.5 cm/s.

The function $\Delta r(t)$ searched, being the instantaneous radius variation, is then obtained, using a subtracter and a divider-by-2, on the basis of the relation:

$$\Delta r(t) = \tfrac{1}{2}(D_2(t) - D_1(t))$$

which relation characterizes the symmetrical shift of the artery walls (dilation or contraction). The results obtained in the form of digital samples are themselves also applied to the first storage means or memory 23.

The elements 21 to 25 form a first assembly for measuring Q(t), $r_0(t)$, $\Delta r(t)$ on the basis of the ultrasonic ethos produced in the artery 1 by the excitation A.

In accordance with the invention, a second excitation line B is formed, starting from the transducer 11, in the same direction z and in the immediate vicinity of the excitation line A. The distance e separating the lines A and B in the direction of the axis of the artery is typically between a few tenths of a millimeter and a few millimeters. The choice of e is governed by the systolic propagation wavelength $\lambda$ along the arteries, $\lambda$ being of the order of 0.5 m. e must be substantially smaller than $\lambda$, justifying the choice of distances which are from 100 to 1000 times smaller.

Depending on the echographic equipment used, as described hereinafter with reference to the FIGS. 3 and 4 the excitations A and B can either be simultaneous or be spaced slightly apart by a period $\tau$ which is small in comparison with the duration $T_c$ of a cardiac cycle. This causes a second output signal S'(t,z) of the transmission-receiving means 12, more precisely from the channel forming device 10, which second signal is applied to a second assembly for measuring Q'(t) and $\Delta r'(t)$, which is similar to the first assembly for measurement described above (the measurement of $r_0$, already calculated by the first assembly, is useless in this case). After processing in the blocks 31, 32, 35, identical to the blocks 21, 22, 25, the blood flow rate Q'(t) and the instantaneous variation of the radius $\Delta r'(t)$ are applied, in the form of digital samples, to the second storage means 33.

Calculation means (calculator) 41, performing data processing, enable determination, on the basis of the digital samples stored in 23 and 33, of the physiological parameters which are characteristic of the artery analysed, notably the elasticity $\gamma(t)$ which is defined as:

$$\gamma(t) = \frac{dr(t)}{dP(t)} \quad (3)$$

and the internal pressure P(t) as will be described hereinafter. It is to be noted that in the case of non-simultaneous excitations A and B, rephasing between samples stored in the memories 23 and 33 is the first operation to be performed by the calculator 41, the dephasing to be corrected being equal to $2\pi\tau/T_c$ ($t_c$ being the period of the cardiac cycle).

Figure 2:
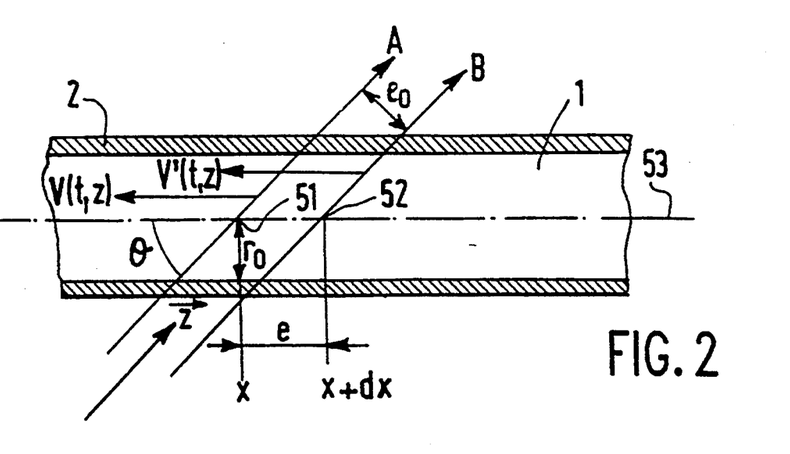
FIG. 2 is a diametrical sectional view of a part of an artery with two neighbouring ultrasonic excitation lines.

For the sake of clarity, FIG. 2 shows at an increased scale a part of an artery in the echographic analysis region in accordance with the invention. This region is bounded by two radial planes x and x+dx which extend through the points of intersection 51 and 52 of the excitation lines A and B with the axis 53 of the artery, the parallel lines A and B defining a meridian plane of the artery which is chosen as the sectional plane of the Figure. These two planes are separated by the distance $$\frac{e_0}{\sin\theta},$$

where $e_0$ is the distance between the two lines A and B and $\theta$ is the angle enclosed by the direction of the artery relative to the direction z of the two excitation lines. Depending on the value chosen for $e_0$ and the value of $\theta$, the distance e is between a few tenths of a millimeter and a few millimeters. The Figure also shows the point blood speeds V(t,z) and V'(t,z), measured in the artery whose passage, or internal section, is: $S = \pi r^2$ (mean section: $S_0 = \pi r_0^2$).

Figure 3:
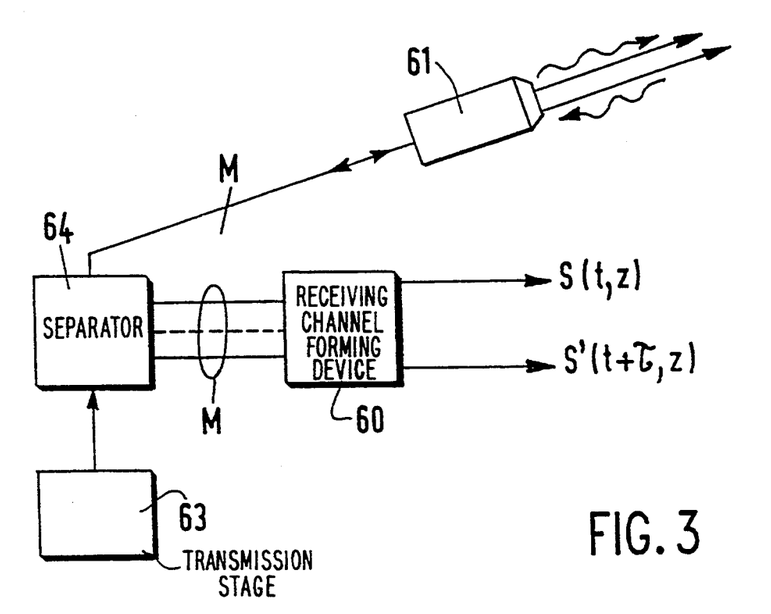
FIGS. 3 and 4 show partial circuit diagrams of a first and a second specific embodiment of the device in accordance with the invention.
Figure 4:
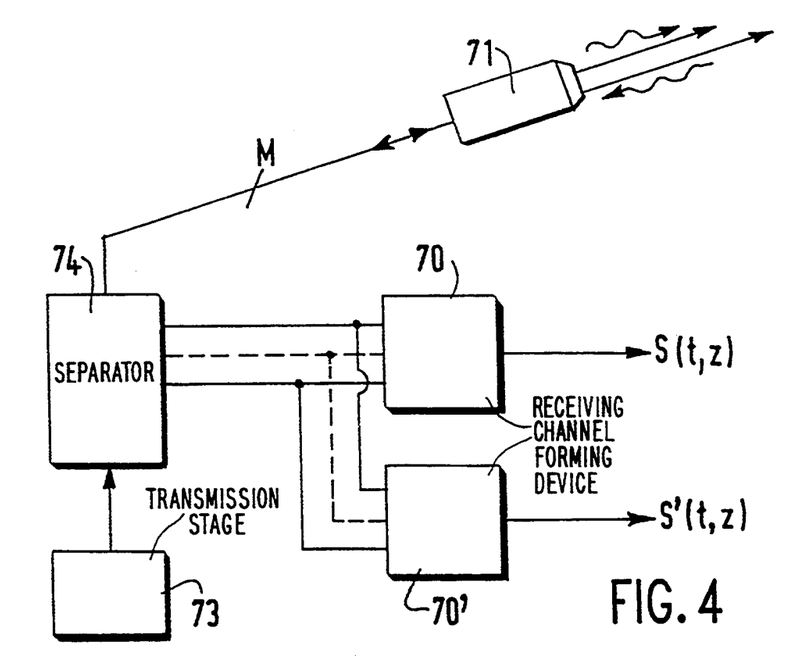

FIGS. 3 and 4 show two specific embodiments of the device in accordance with the invention.

The essence of the construction of the echograph shown in FIG. 3 may be considered to be known as it can be simply deduced from an echograph which is known as a CVI (Colour Velocity Imaging) echograph. The CVI application concerns the formation, using 128 elementary transducers, of an echographic image which consists of, for example, 128 coplanar parallel lines, whose points for which the speeds exceed predetermined thresholds in the positive and negative sense are denoted by different colours (the case of blood in the veins and the arteries which approaches or moves away from the ultrasonic probe). Preferably, the number of lines to be analysed equals the number of M elementary transducers. The image lines are successively formed in the order of their sequence numbers. However, in order to adapt the measuring frequency of the successive points of each line to the (blood) speed ranges to be measured, an optimum approach is to proceed with 2, 3 or 4 successive image lines simultaneously (followed by the formation of the next 2, 3 or 4 lines). For the formation of two adjacent lines (typically spaced 0.45 mm apart), necessitating several excitations, a point of a first line is determined, followed by the corresponding point of the second line, after a period $\tau$, followed by the next point of the first line, after a period $2\tau$, and so on for all points of these two lines. To this end, the receiving channel forming device 60, receiving the M echo signals from the transducer 61 via the separator 64 which is controlled by the transmission stage 63, reconfigures its delays at each instant $\tau$, now on the first line and then on the next line. The signals obtained for the two said lines suffice for carrying out the present invention. These signals, multiplexed in known manner in 60, are denoted as S(t,z) and S'(t+τ,z) at the output of the channel forming device 60. The output signals must be strictly simultaneous for the corresponding points of the analysed pair of lines. Consequently, rephasing amounting to $2\pi\tau/T_c$ is performed, after processing of the signals, between the digital samples contained in the memory 33 (FIG. 1) and those stored in the memory 23.

By selectively using the CVI mode of operation for the lines, it is also possible to combine two neighbouring lines which are separated by twice the pitch of the lines (0.9 mm), the dephasing to be corrected being equal to $4\pi\tau/T_c$, or three times this pitch (1.35 mm) in which case the dephasing to be corrected amounts to $6\pi\tau/T_c$. For the characterization of an atheroma or a stenosis, in accordance with the present invention several successive pairs of lines can be analysed, without displacement of the probe, so as to determine the compliance $\gamma$ and the pressure P at a plurality of points of the artery which are situated near one another over an axial distance of the order of from 1 to 3 cm.

The operation of the embodiment shown in FIG. 4 is simpler than that of the embodiment shown in FIG. 3. It concerns essentially a profilometer, originally conceived to realise a single excitation line by means of a transducer 71 comprising M elementary transducers, a transmission stage 73, a separator 74 and a channel forming device 70 which supplies the signal S(t,z). This profilometer is adapted to supply, in the receiving mode, a second analysis line S'(t,z) which neighhours and extends parallel to the first analysis line. To this end, it is first of all necessary to transmit a beam which is slightly wider, that is to say slightly defocused, and slightly less powerful than in the event of a conventional profilometer. The slight defocusing is hardly detrimental in as far as the precision required for the measurement of the analysed points is concerned. Defocusing is achieved simply by suitable control in 71 of the electronic scanning (not shown) of the elementary transducers during the pulse excitations. Using the described adapted transmission, a second channel forming device 70', receiving the same signals as the device 70 and utilizing a delay configuration slightly shifted with respect to that of the device 70, enables the formation of a second analysis line in the receiving mode, which second line extends adjacently and parallel to the first line and can be identified by the output signal S'(t,z). In this embodiment, the second line is obtained simultaneously with the first line in a sense that each pair of corresponding points of the two lines is supplied at the same instant at the output of the devices 70 and 70'. The time shift between the delay configurations applied in the channel forming devices 70 and 70' could be rendered adjustable, becoming manifest as a variation of the distance e which is deduced directly from this time shift. The doubling of the channel forming devices renders the device shown in FIG. 4 more expensive than that shown in FIG. 3 even though, in this case, the time locking of the corresponding points of the two lines is no longer necessary.

It is an object of the invention to measure the elasticity $\gamma$ of an artery under the influence of the blood pressure P, on the basis of digital samples stored in the memories 23 and 33 (FIG. 1).

The fundamental equation of the dynamics, transposed to the circulatory system, for the blood flow can be written as:

$$F_R + dx\, \rho \frac{dV}{dt}\, dS = [-P(x+dx) + P(x)]dS$$

where:
- $\rho$: voluminal mass of blood
- $V = V(t,x)$: speed of the blood
- $P = P(t,x)$: blood pressure
- $F_R$: friction forces.

By integration with respect to S and after division by S and by dx there is obtained:

$$F_{R'} + \frac{\rho}{S}\int_S \frac{dV}{dt}\, dS = -\frac{dP}{dx} \tag{5}$$

Since:

$$\frac{dV}{dt} = \frac{\partial V}{\partial t} + V\frac{\partial V}{\partial x}$$

the relation (5) can be written as:

$$RQ + L\left[\frac{\partial Q}{\partial t} + \frac{\partial \sqcup}{\partial x}\right] = -\frac{dp}{dx} \tag{6}$$

where:
- $Q = Q(t,x)$: blood flow rate
- R: hydrodynamic resistance taking into account the friction on the arterial wall and the viscosity of blood
- $L = \rho/S$
- $\sqcup = \tfrac{1}{2}\int V^2 dS$ For the continuation of the calculations, the function $\sqcup(x)$ is assumed, with a very good approximation, to be a constant in the case of blood, so that:

$$\frac{\partial \sqcup}{\partial x} \simeq 0$$

and the simplified relation (6) becomes:

$$RQ + L\frac{\partial Q}{\partial t} = -\frac{dP}{dx} \tag{7}$$

It is to be noted that, using this simplification, a single function from among Q(t) or Q'(t) suffices for the continuation of the calculations.

The pressure P also acts on the arterial walls and dilates or compresses these walls, involving their elasticity or compliance $\gamma$ which is an essential parameter describing the performance of the arterial system. With regard to the artery walls the following can be written:

$$\frac{dP}{dx} = \frac{\partial P}{\partial x} + \frac{\partial P}{\partial S}\frac{\partial S}{\partial x} = \frac{\partial P}{\partial x} + \frac{\partial P}{\partial r}\frac{\partial r}{\partial x}$$

so, for:

$$\gamma = \frac{\partial r}{\partial P} \text{ and assuming } \frac{\partial P}{\partial x} = \frac{\Delta P}{\Delta x}$$

for the relation (7):

$$\gamma\left[RQ + L\frac{\partial Q}{\partial t} + \frac{\Delta P}{\Delta x}\right] = -\frac{\partial r}{\partial x} \quad (8)$$

The invention is based on the physical possibility to measure the quantities r(x) and r(x+dx) with a precision which suffices for their difference to be rather significant. In practice, the precision of this instantaneous difference can be obtained on the basis of the expression:

$$\delta r(t) = \Delta r(t) - \Delta r'(t)$$

and, in the relation (8) the following identification is made:

$$\frac{\partial r}{\partial x} = \frac{\delta r(t)}{e} \quad (9)$$

It is to be noted that the quantity dx/dt=e/dt is the propagation speed of the systolic wave along the artery (of the order of 6 m/s) and not the blood speed within the artery, so that for a value e of 0.45 mm the value dt=75 μs, which justifies the existence of a value δr which can be measured with such a small value of dx.

In the relation (8) there are first calculated the quantities δQ/δt (on the basis of the known function Q(t)) and −δr/δx (in accordance with the equality (9)).

It is now proposed to estimate first of all the mean values of the parameters γ, R and ΔP/Δx which are denoted as $\gamma_0$, $R_0$ and $$\left(\frac{\Delta P}{\Delta x}\right)_0$$

ΔP/Δx represents the continuous component of the function $$\frac{dP(x,t)}{dx},$$

that is to say the mean pressure gradient along the artery which is generated by the mean flow rate $Q_0 = <Q(t)>$ which can be calculated on the basis of the function Q(t), so: $R_0 Q_0$. Moreover, the variation of r being small over the distance e, it can be assumed that:

$$L = L_0 = \frac{\rho}{\Pi r_0^2} \text{ (in 9, mm).}$$

This estimate is preferably made by way of the least-squares method, meaning minimization of the square of the norm:

$$\left\| T_1(Q) + \frac{\partial r}{\partial x} \right\|^2$$

where:

$$T_1(Q) = \gamma\left[R Q + L_0\frac{\partial Q}{\partial t} + R Q_0\right]$$

Three equations follow therefrom with the partial derivatives:

$$\frac{\partial}{\partial var}\left(\left\| T_1(Q) + \frac{\partial r}{\partial x} \right\|^2\right) =$$

$$2 < \frac{\partial T_1(Q)}{\partial var} \cdot \left(T_1(Q) + \frac{\partial r}{\partial x}\right)> = 0$$

with, successively, var=γ, R and $RQ_0$. When all calculations have been made, the following is deduced therefrom (the mean values having been taken over the duration $T_c$ of a cardiac cycle):

$$\gamma_0 = \frac{1}{L_0}\frac{<\frac{\partial Q}{\partial t} \times \frac{\partial r}{\partial x}>}{<\frac{\partial Q^2}{\partial t}>} = \frac{b}{L_0} \text{ (in g, mm, s)}$$

The compliance is preferably expressed in microns per millimeter of mercury height (μ/mm Hg), so that for $\rho = 10^{-3}$ g/mm$^3$:

$$\gamma_0 = 419.14 \times 10^3 \, r_0^2 \, b \, \mu/\text{mm Hg } (r_0, b \text{ in mm, s})$$

The values found for $\gamma_0$ are of the order of 1μ for 40μ mercury. Moreover, said least-squares method provides the relation:

$$a = \gamma_0 R_0 = -\frac{<Q \times \frac{\partial r}{\partial x}>}{<Q^2>}$$

It follows therefrom that:

$$R_0 = \frac{a}{\gamma_0} = L_0\frac{a}{b} = -L_0\frac{<Q \times \frac{\partial r}{\partial x}> \times <\frac{\partial Q^2}{\partial t}>}{<Q^2> \times <\frac{\partial Q}{\partial t} \times \frac{\partial r}{\partial x}>}$$

and:

$$\left(\frac{\Delta P}{\Delta x}\right)_0 = R_0 Q_0 = \frac{a}{\gamma} Q_0$$

and also:

$$\left(\frac{\Delta P}{\Delta x}\right)_0 = \frac{1}{419.14} \times \frac{Q_0}{r_0^2} \times \frac{a}{b} \text{ mm Hg/mm}$$

For a healthy artery the pressure gradient $R_0Q_0$ is substantially constant along the entire artery, that is to say from the heart as far as the organs. However, at the area of a stenosis, the pressure gradient will be substantially higher than at other points of the artery. The determination of this gradient as indicated above enables the radiologist to localize exactly a stenosis and to map it by repeating the described measurements several times at intervals of a few millimeters along the altered part of the artery, so that a profile of the pressure gradient can be obtained. It is thus also feasible to envisage, using a non-invasive process, which types of care or intervention (angioplasty) are suitable for the treatment of said stenosis. An aneurysm can thus also be detected with high precision.

If the mean value of the pressure gradient already constitutes a very exact indication, however, it may be desirable to know the variation as a function of time of the functions R(t) and γ(t) in the course of the cardiac cycle. This can be achieved, on the basis of the previously determined mean values $L_0$, $\gamma_0$, $R_0$ and $R_0Q_0$, by applying the least-squares method again, be it not over the entire duration of a cardiac cycle but for two half-cycles and then by successive iterations for four, eight, . . . , parts of a cycle. To this end, a start is made from the relation (8) in which it is assumed that:

$$R = R_0(1 + R'(t))$$
$$\gamma = \gamma_0(1 + g'(t))$$
$$\frac{\partial r}{\partial x} = \frac{\delta r(t)}{e}$$

so:

$$\gamma_0(1 + g'(t)) \left[ R_0(1 + R'(t)) Q(t) + L_0 \frac{\partial Q}{\partial t} + R_0 Q_0 \right] = -\frac{\delta r(t)}{e}$$

This method provides functions γ(t) and R(t) which are constant in segments γ and R, that is to say in the form of a few samples over the duration of the cardiac cycle.

It is to be noted that the calculations are in this case complicated by the fact that given functions which were zero on average over the duration of the cardiac cycle for the calculation of $\gamma_0$ and $R_0$ are no longer zero on average over a part of the cycle.

The compliance as a function of time being known by way of its approximated function γ(t), the internal pressure in the artery can be calculated as a function of time P(t) by integration on the basis of the definition of the compliance γ itself:

$$\gamma = \frac{\partial r}{\partial P} \quad (3)$$

so:

$$\frac{\partial P}{\partial t} = \frac{1}{\gamma} \frac{\partial r}{\partial t} \quad (2)$$

and:

$$P_1(t) = \int_t \frac{\partial P}{\partial t} dt = \int_t \frac{1}{\gamma(t)} \frac{\partial r}{\partial t} dt \quad (11)$$

The notation $P_1(t)$ expresses the fact that the pressure P(t) searched is obtained, subsequent to the integration, except for a constant additive or continuous component $P_c$:

$$P_c = <P_1(t)>$$

(mean value calculated over a cardiac cycle).

If it is assumed that:

$$P(t) = P_0 + p(t),$$

the variable part p(t) of the pressure P(t) is obtained as the difference:

$$p(t) = P_1(t) - <P_1(t)> \quad (12)$$

The mean value or fixed part $P_0$ is obtained by utilizing the tension T(t), in the physical sense (and not the medical) sense of the word, exerted by the blood on a circumference of the artery:

$$P(t) - P_e = T(t)/r(t) \text{ (transmural pressure)} \quad (13)$$

where $P_e$: pressure outside the artery, being constant and of the order of magnitude of atmospheric pressure.

By derivation with respect to time there is obtained:

$$\frac{\partial P}{\partial t} = \frac{1}{r} \frac{\partial T}{\partial t} - \frac{1}{r^2} \frac{\partial r}{\partial t} T \quad (14)$$

in which: P=P(t), T=T(t) and r=r(t). So, by multiplication by r and by taking into account the equation (2) there is obtained:

$$\frac{\partial T}{\partial t} - \frac{1}{r} \frac{\partial r}{\partial t} T = \frac{r}{\gamma} \frac{\partial r}{\partial t}$$

The least squares method is used again. In order to minimize the square of the norm:

$$\left\| T_2(T) - \frac{r}{\gamma} \frac{\partial r}{\partial t} \right\|^2$$

where:

$$T_2(T) = \frac{\partial T}{\partial t} - \frac{1}{r} \cdot \frac{\partial r}{\partial t} T$$

Two equations are then obtained with the partial derivatives:

$$\frac{\partial}{\partial var} \left( \left\| T_2(T) - \frac{r}{\gamma} \frac{\partial r}{\partial t} \right\|^2 \right) =$$

$$2 < \frac{\partial T_2(T)}{\partial var} \cdot \left( T_2(T) - \frac{r}{\gamma} \frac{\partial r}{\partial t} \right) > = 0$$

with, successively: var=δT/δt and var=T.

Once all calculations have been completed, the mean value $T_0$ of T is deduced therefrom at this stage by making the simplification: $\gamma = \gamma_0$:

$$T_0 = \frac{1}{\gamma_0} \frac{<r \frac{\partial r}{\partial t}><\frac{1}{r} \frac{\partial r}{\partial t}> - <\left(\frac{\partial r}{\partial t}\right)^2>}{<\left(\frac{1}{r} \frac{\partial r}{\partial t}\right)^2> - <\frac{1}{r} \frac{\partial r}{\partial t}>^2} \quad (15)$$

It follows that:

$$P_0 = P_e + T_0/r_0$$

from which it is finally deduced that:

$$P(t) = P_1(t) - <P_1(t)> + P_e + T_0/r_0$$

Depending on the function chosen for the radius r(t) (side x) or r'(t) (side x+dx), there is thus obtained the pressure P(t) at the point 51 (FIG. 2) or at the point 52. It is also to be noted that the functions δr/δt can be obtained by direct derivation from the functions Δr(t)

or $\Delta r'(t)$ in as far as the calculations of the mean values in accordance with the relation (15), are concerned.

I claim:

1. A device for measuring physiological parameters of an artery containing flowing blood having an instantaneous pressure P(t), said device comprising, in an ultrasonic echograph used in profilometer mode (M mode) and provided with transmission/receiving means including a device for forming channels in a receiving mode, a first assembly for measuring and forming at outputs of the first assembly a first set of signals representing an instantaneous blood flow rate Q(t) within the artery, an instantaneous radius variation $\Delta r(t)$ of the artery, and a mean radius $r_0$ of the artery along a first excitation line A, characterized in that it also comprises, for the determination of elasticity $\gamma(t)$ of said artery and the pressure P(t) of the flowing blood within the artery, a second assembly for measuring, by ultrasonic echography, and forming at its outputs a second set of signals representing an instantaneous blood flow rate Q'(t) and an instantaneous radius variation $\Delta r'(t)$ along a second excitation line B neighbouring the first excitation line A, the second excitation line B being situated at a distance e from the first excitation line A, which distance is small in comparison with the systolic propogation wavelength $\lambda$ along the artery, the two excitation lines A and B traversing the artery according to one of its meridian planes, the distance e being taken in the direction of the axis of the artery, first and second storage means connected to the respective outputs of said first and second assemblies for storing digital samples of said respective first and second sets of signals and calculation means coupled to said first and second storage means for operating on said stored digital samples to calculate physiological parameters of said artery.

2. A device for measuring physiological parameters of an artery as claimed in claim 1, characterized in that it comprises transmission/receiving means of an ultrasonic echograph operating to detect by ultrasonic lines by time correlation and intended to produce ultrasonic images in two-dimensional mode, its detection being limited to the two neighbouring excitation lines A and B which are separated by the distance e, and taking place in pairs of homologous points of the two excitation lines, as well as means for rephasing the signals received for said two neighbouring excitation lines, which means are integrated in said calculation means.

3. A device for measuring physiological parameters of an artery as claimed in claim 2, wherein the distance e is less than or equal to 5 mm.

4. A device for measuring physiological parameters of an artery as claimed in claim 1, characterized in that it is formed by an ultrasonic echograph operating to detect signals of ultrasonic lines by time correlation and used as a profilometer in which the transmission means are suitable to transmit a more powerful and slightly defocused ultrasonic beam in comparison with that of a conventional profilometer, the device incorporating two channel forming devices for forming in parallel and simultaneously at their respective outputs, detected signals of said two excitation lines A and B which are separated by the distance e.

5. A device for measuring physiological parameters of an artery as claimed in claim 1, wherein the distance e is less than or equal to 5 mm.

6. A device for measuring physiological parameters of an artery as claimed in claim 1, wherein the distance e is less than or equal to 5 mm.

7. A method for measuring an elasticity parameter $\gamma$ of an artery within a living subject containing flowing blood having a blood pressure P by irradiating the living subject with ultrasonic radiation along two neighboring, parallel excitation lines traversing the artery according to one of its meridian planes, collecting samples of echo signals returned from said subject and producing from said collected samples, and storing, instantaneous blood flow rates Q(t), Q'(t), and instantaneous radius variations $\Delta r(t)$, $\Delta r'(t)$ for the two neighbouring parallel excitation lines respectively, and a mean radius $r_0$ for the artery, said producing comprising the following steps:

i calculating, on the basis of one of the two functions Q(t), Q'(t), a mean value $Q_0$ and a derivative $$\frac{\partial Q(t)}{\partial t}$$

of the one function, ii calculating, on the basis of the instantaneous values $\Delta r(t)$, $\Delta r'(t)$ for the lines A and B, the instantaneous value:

$$\delta r(t) = \Delta r(t) - \Delta r'(t)$$

iii determining mean values of the elasticity parameter $\gamma$, a hydrodynamic resistance parameter R and a pressure gradient $\Delta P/\Delta x$, i.e. $\gamma_0$, $R_0$ and $R_0 Q_0$, respectively, on the basis of the least squares method applied, over a cardiac cycle, to the relation:

$$\gamma \left[ R \, Q(t) + L \frac{\partial Q(t)}{\partial t} + \frac{\Delta P}{\Delta x} \right] = -\frac{\partial r(t)}{\partial x}$$

in which the identification:

$$L = \frac{\rho}{\Pi r_0^2}, \text{ and } \frac{\partial r(t)}{\partial x} = \frac{\delta r(t)}{e}$$

is made.

8. A method of measuring the elasticity $\gamma$ of an artery as claimed in claim 7, characterized in that for the determination in segments, over at least one cardiac cycle, of the functions $\gamma(t)$ and R(t) the least-squares method is applied again by successive iterations over complementary parts of the cardiac cycle whose number increases, from one iteration to the next by taking, for the first iteration, two cardiac half-cycles (and then 4, 8, ..., parts of cycles for the subsequent iterations), and the relation:

$$\gamma_0 (1 + g'(t)) \left[ R_0 (1 + R'(t)) Q(t) + L \frac{\partial Q}{\partial t} + R_0 Q_0 \right] = -\frac{\delta r(t)}{e},$$

which supplies for $\gamma$ and R the sampled functions of some samples over the duration of the cardiac cycle.

9. A method for measuring the pressure $P(t) = P_0 + P(t)$ within an artery, in which the value of r(t) for one of the excitations A or B is determined on the basis of the values $r_0$ and $\Delta r(t)$ as claimed in claim 5, characterized in that the variable part: p(t) of the pressure is determined by integration with respect to time of the function with the partial derivatives $P_1$:

$$P_1(t) = \int_t \frac{\partial P}{\partial t} dt = \int_t \frac{1}{\gamma(t)} \frac{\partial r}{\partial t} dt$$

followed by suppression of the continuous component $P_c$ of $P_1(t)$:

$$P(t) = P_1(t) - P_c$$

and that the fixed part $P_0$ (to be added to $P(t)$) is determined by application of the least-squares method to the relation:

$$\frac{\partial P}{\partial t} = \frac{1}{r} \frac{\partial T}{\partial t} - \frac{1}{r^2} \frac{\partial r}{\partial t} T$$

in which: $r = r(t)$ and $T = T(t) = r(t) P(t)$, $T(t)$ being the tension, in a physical sense, exerted by the blood on a circumference of the artery, so that therefrom in a first approximation there is deduced:

$$T_0 = \frac{1}{\gamma_0} \frac{\left\langle r \frac{\partial r}{\partial t} \right\rangle \left\langle \frac{1}{r} \frac{\partial r}{\partial t} \right\rangle - \left\langle \left(\frac{\partial r}{\partial t}\right)^2 \right\rangle}{\left\langle \left(\frac{1}{r} \frac{\partial r}{\partial t}\right)^2 \right\rangle - \left\langle \frac{1}{r} \frac{\partial r}{\partial t} \right\rangle^2},$$

in which the symbols $\langle \rangle$ indicate the mean value of the function taken over a cardiac cycle, and:

$$P_0 = T_0/r_0 + P_e$$

$P_e$ being the (constant) pressure outside the artery.

* * * * *